United States Patent [19]

Kreis et al.

[11] 4,177,341

[45] Dec. 4, 1979

[54] ADDITION OF SI-BONDED HYDROGEN TO AN ALIPHATIC MULTIPLE BOND

[75] Inventors: Gerhard Kreis, Munich; Peter August, Burghausen; Manfred Wick, Schliersee, all of Fed. Rep. of Germany

[73] Assignee: Consortium Für Elektrochemische Industrie GmbH, Munich, Fed. Rep. of Germany

[21] Appl. No.: 909,094

[22] Filed: May 24, 1978

[30] Foreign Application Priority Data

Jun. 2, 1977 [DE] Fed. Rep. of Germany ....... 2724822

[51] Int. Cl.$^2$ ............................................. C08G 77/06
[52] U.S. Cl. ...................................... 528/15; 528/31; 528/32; 264/16; 264/19
[58] Field of Search ............... 528/15, 31, 32; 264/19, 264/16

[56] References Cited

U.S. PATENT DOCUMENTS

| 3,723,497 | 3/1973 | Baney | 528/15 |
| 3,950,300 | 4/1976 | Hittmair et al. | 528/15 |

Primary Examiner—Melvyn I. Marquis

[57] ABSTRACT

A process for the addition of Si-bonded hydrogen to an aliphatic multiple bond in the presence of a platinum catalyst selected from the group consisting of

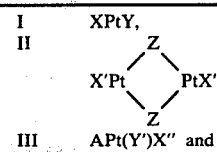

I    XPtY,
II   
III  APt(Y')X" and mixtures thereof, in which A is a halogen, X is a substituted or unsubstituted hydrocarbon radical having from 1 to 3 aliphatic double bonds which is bonded to the platinum atom via a PtC-sigma bond and a Pt-olefin-Pi-bond, X' is a hydrocarbon radical which is substituted with an alkoxy or acyloxy group and has from 1 to 3 double bonds and is bonded to the platinum atom via a PtC-sigma bond and a Pt-olefin-Pi-bond, X" is a substituted or unsubstituted hydrocarbon having an aliphatic double bond which is bonded to the platinum atom via a Pt-olefin-Pi-bond, Y is a chelate-like bonded beta-diketonate ligand or arylcarboxylate ligand, Y' is a beta-diketonate ligand and Z is a double link bridge ligand.

11 Claims, No Drawings

ADDITION OF SI-BONDED HYDROGEN TO AN ALIPHATIC MULTIPLE BOND

The present invention relates to a process for the addition of Si-bonded hydrogen to an aliphatic multiple bond and more particularly to a process for the addition of Si-bonded hydrogen to an aliphatic multiple bond in the presence of a platinum catalyst.

BACKGROUND OF THE INVENTION

Heretofore it has been known that a number of platinum-containing materials will catalyze the addition of silicon-bonded hydrogen atoms across the double bonds of compounds containing olefinic unsaturation. This addition is sometimes referred to as "hydrosilation" and may be illustrated by means of the following equation:

≡SiH + C═C → ≡SiC—CH

Many of the known hydrosilation methods involve the employment of a platinum catalyst in the form of a halogenated platinum compound such as described in U.S. Pat. No. 2,823,218 to Speier which utilizes chloroplatinic acid as the platinum catalyst. Other hydrosilation methods involve the employment of platinum catalysts in the form of platinum-vinylsiloxanes which are substantially free of chemically combined halogen such as described in U.S. Pat. Nos. 3,715,334; 3,775,452 and 3,814,730 to Karstedt. Additional methods are shown in U.S. Pat. Nos. 3,159,601 to Ashby and 3,723,497 to Baney.

Although the above-described platinum materials catalyze the addition of silicon-bonded hydrogen atoms to aliphatic double bonds, the catalysts of this invention are substantially more effective than the catalysts known heretofore. Thus, in order to achieve the same results, smaller amounts of platinum may be employed in the process of this invention when using the catalysts described herein as compared to the catalysts known heretofore. In otherwords, when the same amount of platinum is used in the process of this invention, the reaction time is substantially less than when the catalysts known heretofore were employed in the hydrosilation methods.

Therefore, it is an object of this invention to provide for the platinum catalyzed addition of silicon-bonded hydrogen atoms to compounds containing aliphatic multiple bonds. Another object of this invention is to provide a hydrosilation method which utilizes a platinum catalyst that is substantially more effective than the platinum catalysts used heretofore. A further object of this invention is to provide a process for the addition of silicon-bonded hydrogen atoms to compounds containing aliphatic multiple bonds.

SUMMARY OF THE INVENTION

The foregoing objects and others which will become apparent from the following description are accomplished in accordance with this invention, generally speaking, by mixing a silicon compound containing Si-bonded hydrogen with compounds containing an aliphatic multiple bond in the presence of a platinum catalyst selected from the class consisting of

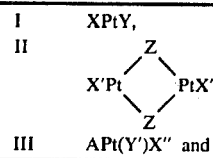

I   XPtY,
II  
III APt(Y')X''  and mixtures thereof, in which A is a halogen, X is a substituted or unsubstituted hydrocarbon radical having from 1 to 3 aliphatic double bonds which is bonded to the platinum atom via a PtC-sigma bond and a Pt-olefin-Pi bond, X' is a hydrocarbon radical which is substituted with an alkoxy or acyloxy group and has from 1 to 3 double bonds and is bonded to the platinum atom via a PtC-sigma bond and a Pt-olefin-Pi-bond, X'' is a substituted or unsubstituted hydrocarbon having an aliphatic double bond which is bonded to the platinum atom via a Pt-olefin-Pi bond, Y is a chelate-like bonded beta-diketonate ligand or arylcarboxylate ligand, Y' is a beta-diketonate ligand and Z is a double link bridge ligand.

DETAILED DESCRIPTION OF THE INVENTION

The radicals represented by X and X' which may be the same or different, are substituted or unsubstituted hydrocarbon radicals. Preferably, these hydrocarbon radicals have only one aliphatic double bond. Examples of groups which may be linked to the hydrocarbon radicals X are the acetylacetonyl radical, as well as alkoxy and acyloxy groups having from 1 to 3 carbon atoms. It is preferred that the alkoxy or acyloxy groups linked to the hydrocarbon radicals X' have from 1 to 3 carbon atoms. Furthermore it is preferred that Z be $Cl^-$ or $RCOO^-$ radicals, where R is a hydrocarbon radical and more preferably a hydrocarbon radical having from 1 to 3 carbon atoms, such as for example, the methyl, ethyl, n-propyl, isopropyl, vinyl or allyl radical. Because of their availability, it is preferred that A be chlorine and that X'' be ethylene.

Compounds represented by class (I) and their methods of preparation are described for example by B. F. G. Johnson and associates in the "Journal of the Chemical Society", section A, 1968, pages 1993 to 2001, as well as by J. K. Stille and associates, in the "Journal of the American Chemical Society", Volume 92, 1970, pages 1274 to 1278. Excellent results are obtained using a compound having the following formula:

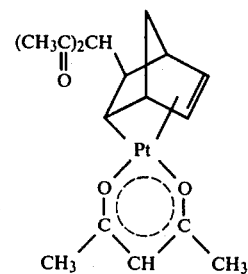

which may be referred to as "(acac-$C_7H_8$)Pt(acac)".

Compounds represented by class (II) and their methods of preparation are described for example by J. Chatt and associates, in the "Journal of the Chemical Society", 1957, pages 2496 to 2505. Excellent results are obtained with a compound corresponding to the following formula:

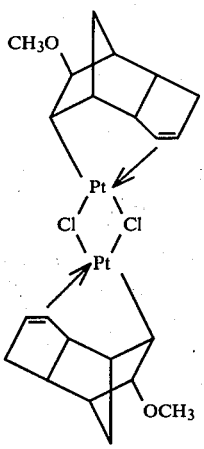

which may be referred to as "[(CH$_3$O-C$_{10}$H$_{12}$)PtCl]$_2$".

Compounds represented by Class (III) and their methods of preparation are described for example by C. E. Holloway and associates in the "Journal of the Chemical Society", section A, 1970, pages 1653 to 1658. Outstanding results are achieved using acetylacetonato-chloro(ethylene)-platinum-(II) which can be abbreviated as "(C$_2$H$_4$)PtCl(acac)".

Examples of compounds relating to class (I) having chelate-like bonded beta-diketonate ligands are the following:

| | |
|---|---|
| (acac-C$_7$H$_8$)Pt(acac) | (Bzac-C$_7$H$_8$)Pt(Bzac) |
| (acac-C$_8$H$_{12}$)Pt(acac) | (Bzac-C$_8$H$_{12}$)Pt(Bzac) |
| (acac-C$_{10}$H$_{12}$)Pt(acac) | (Bzac-C$_{10}$H$_{12}$)Pt(Bzac) |
| (RO-C$_7$H$_8$)Pt(acac) | (dbm-C$_8$H$_{12}$)Pt(dbm) |
| (RO-C$_8$H$_{12}$)Pt(acac) | (dbm-C$_7$H$_8$)Pt(dbm) |
| (Etac-C$_{10}$H$_{12}$)Pt(Etac) | |

Examples of compounds of class (I) having chelate-like bonded arylcarboxylate ligands are the following:

(C$_6$H$_5$COO—C$_7$H$_8$)Pt(C$_6$H$_5$COO)

(o-,m-,p-CH$_3$C$_6$H$_4$COO—C$_7$H$_8$)Pt(o-,m-,p-CH$_3$C$_6$H$_4$COO)

(C$_6$H$_5$COO—C$_{10}$H$_{12}$)Pt(C$_6$H$_5$COO)

(o-,m-,p-CH$_3$C$_6$H$_4$COO—C$_{10}$H$_{12}$)Pt(o-,m-,p-CH$_3$C$_6$H$_4$COO)

Additional examples of compounds of class (II) are:

[(RO—C$_7$H$_8$)PtCl]$_2$

[(RO—C$_8$H$_{12}$)PtCl]$_2$

[(RO—C$_{10}$H$_{12}$)PtCl]$_2$

[(RO—C$_7$H$_8$)PtBr]$_2$

[(CH$_3$COO—C$_7$H$_8$)Pt(CH$_3$COO)]$_2$

[(CH$_3$COO—C$_8$H$_{12}$)Pt(CH$_3$COO)]$_2$

[(CH$_3$COO—C$_{10}$H$_{12}$)Pt(CH$_3$COO)]$_2$

[(RO—C$_6$H$_{10}$)PtCl]$_2$

Examples of compounds of class (III) are the following:

(C$_2$H$_4$)PtCl(acac)

(C$_2$H$_4$)PtCl(Bzac)

(C$_2$H$_4$)PtCl(3Facac)

(C$_2$H$_4$)PtBr(acac)

(C$_3$H$_6$)PtCl(acac)

(C$_3$H$_6$)PtCl(Bzac)

(C$_3$H$_6$)PtCl(3Facac)

(CH$_2$=CHOH)PtCl(acac)

In the preceding examples of compounds of classes (I), (II) and (III) the above abbreviations represent the following radicals:
acac=acetylacetonate radical
Bzac=benzoylacetonate radical
3Facac=trifluoroacetylacetonate radical
dbm=dibenzoylmethyl radical
Etac=ethylacetoacetate radical
R=CH$_3$, C$_2$H$_5$ or n-C$_3$H$_7$
C$_7$H$_8$=norbornadiene
C$_8$H$_{12}$=1.5-cyclooctadiene
C$_{10}$H$_{12}$=dicyclopentadiene
C$_6$H$_{10}$=Hexadiene-(1.5)
o-,m-,p-,=ortho, meta or para-substitution on the benzene ring The "hydrosilation" of this invention could be described as the addition of a silicon compound having Si-bonded hydrogen to compounds containing an aliphatic multiple bond. The amounts of catalyst used in the process of this invention may be the same as those which have been used heretofore in the addition of Si-bonded hydrogen to an aliphatic multiple bond in the presence of a platinum catalyst. Generally, the amount of catalyst is at least 10$^{-10}$ gram atom, and more preferably from 10$^{-8}$ to 10$^{-3}$ gram atom of platinum, calculated as elemental platinum, for each gram atom of Si-bonded hydrogen. Nevertheless, it should be noted that smaller amounts of catalyst, calculated as elemental platinum, are required in the instant process than were required in the processes known heretofore for the addition of Si-bonded hydrogen to an aliphatic multiple bond in the presence of platinum catalyst under identical conditions, i.e., temperature and time.

The pressures and temperatures used in the process of this invention may be the same as those which were used in the processes known heretofore for the addition of Si-bonded hydrogen to an aliphatic multiple bond in the presence of a platinum catalyst. The process is generally carried out at temperatures between room temperature and 150° C. and at atmospheric pressure, i.e., 760 mm Hg (abs.) or approximately 760 mm Hg (abs.).

The process of this invention may be used whenever monomeric or polymeric silicon compounds having Si-bonded hydrogen are to be added to monomeric or polymeric compounds having an aliphatic multiple bond. Depending upon which compounds are to be added, the addition can produce other monomeric compounds. For example 3-chloropropyltrichlorosilane can be prepared by reacting trichlorosilane with allyl chloride, or n-propyltrichlorosilane can be prepared by reacting propene with trichlorosilane. Also methacryloxypropyltrichlorosilane can be prepared by the addition of trichlorosilane to allylmethacrylate or vinylmethyldichlorosilane can be prepared by reacting acetylene with methyldichlorosilane. In addition, modified dimeric or polymeric compounds containing silicon can be prepared by the addition of Si-bonded hydrogen to compounds containing aliphatic multiple bonds. For example, vinyltrichlorosilane can be reacted with trichlorosilane to form bis-(1,2-trichlorosilyl)-ethane. Also the number of aliphatic multiple bonds in polymers, for example poly(oxyalkylene)polyols, can be decreased by reacting polymers containing aliphatic multiple bonds with organopolysiloxanes having at least two Si-bonded hydrogen atoms per molecule.

Surprisingly, the platinum catalysts used in accordance with this invention are more effective during crosslinking, i.e., curing or vulcanization of compounds which contain alkenyl groups, especially vinyl groups, and organopolysiloxanes containing Si-bonded hydrogen. Consequently, the process of this invention is preferred for the crosslinking of such compounds which may for example be used as potting or coating substances, including substances used for adhesive repellent coatings, on for example, paper or molds especially those used in the pouring of concrete. These catalysts are especially effective in the preparation of materials used for making human or animal dental impressions.

When the platinum catalysts are used in accordance with this invention for cross-linking organopolysiloxane compositions, the organopolysiloxane composition contains (a) an organopolysiloxane containing preferably at least two alkenyl groups and (b) organohydrogenpolysiloxanes having silicon-bonded hydrogen atoms.

Organopolysiloxanes (a) containing alkenyl groups are known in the art and are described, for example in U.S. Pat. Nos. 3,723,497 and 3,950,300. Suitable examples of organopolysiloxanes are preferably diorganopolysiloxanes having triorganosiloxy terminal groups having at least one vinyl group in each terminal unit. These organopolysiloxanes have a viscosity of from about 500 to 300,000 cs. and more preferably from about 2000 up to about 100,000 cs. at 25° C.

The organohydrogenpolysiloxanes (b) containing silicon-bonded hydrogen atoms are described, for example in U.S. Pat. Nos. 3,723,497 and 3,950,300. Preferably these organohydrogenpolysiloxanes have at least three silicon-bonded hydrogen atoms per molecule. Generally, these organohydrogenpolysiloxanes contain from about 0.01 to about 1.7 percent by weight of silicon-bonded hydrogen atoms and the silicon valences not satisfied by hydrogen atoms and siloxane oxygen atoms are satisfied by substituted and unsubstituted monovalent hydrocarbon radicals free of aliphatic unsaturation.

The relative amount of components (a) and (b) employed are such that from 0.75 to 5 gram atoms of silicon-bonded hydrogen are present from component (b) per gram molecule of alkenyl group present from component (a).

In order to prepare a cross-linkable composition, components (a) and (b) and optionally other additives are normally mixed with the platinum catalyst at environmental temperatures and pressures i.e., from about room temperature and about 760 mm Hg (abs.).

In the examples, all parts and percentages are by weight unless otherwise specified.

EXAMPLE 1—Mixture A

About 400 grams of a mixture consisting of 150 parts of a dimethylpolysiloxane having vinyldimethylsiloxy terminal groups and a viscosity of 1200 cP at 23° C., 68 parts of a dimethylpolysiloxane having vinyldimethylsiloxy terminal groups and a viscosity of 22,000 cP at 23° C., 174 parts of cristobalite meal and 8.6 parts of a commercially available treated silicon dioxide pyrogenically produced in the gaseous phase and having a surface area of 200 m$^2$/gm, which has been rendered about 60 percent hydrophobic by reacting with dimethyldichlorosilane, are mixed with 1.6 grams of a 1 percent platinum (calculated as the element) solution of (acac—$C_7H_8$)Pt(acac) in methylene chloride, so as to form a mixture which contains 40 ppm of platinum, (calculated as the element).

Mixture B

About 60 parts of the dimethylpolysiloxane having vinyldimethylsiloxy terminal groups and a viscosity of 1200 cP at 23° C. are mixed with 31 parts of the dimethylpolysiloxane having vinyldimethylsiloxy terminal groups and a viscosity of 22,000 cP at 23° C., 83 parts of cristobalite meal, 5 parts of the treated silicon dioxide described in the preparation of mixture A, and 25 parts of a copolymer having a viscosity of 7700 cP at 23° C. and consisting of dimethylsiloxane, methylhydrogensiloxane and trimethylsiloxane units, with the molar ratio of the dimethylsiloxane units to the methyldrogensiloxane units being 9:1.

Mixtures A and B are stored at room temperature for 3 days and then mixed together in a weight ratio of 1:1. At room temperature, the time elapsed between the mixing of mixtures B and A and the crosslinking of the compounds is 50 seconds.

EXAMPLE 2

The procedure described in Example 1 is repeated, except that 1.6 grams of a 1 percent platinum solution (calculated as the element) of [($CH_3O$—$C_{10}H_{12}$)$PtCl$]$_2$ is substituted for (acac-$C_7H_8$)Pt(acac).

At room temperature, the elapsed time between the initial addition of mixture B and mixture A and observable cross-linking of the composition is 70 seconds.

EXAMPLE 3

The procedure described in Example 1 is repeated, except that 1.6 grams of a 1 percent platinum solution (calculated as the element) of ($C_2H_4$)PtCl(acac) in methylene chloride is substituted for (acac-$C_7H_8$)Pt(acac).

At room temperature, the elapsed time between the initial addition of mixture B to mixture A and observable cross-linking is 30 seconds.

Comparison Example a

The procedure described in Example 1 is repeated, except that 1.6 grams of a 1 percent platinum solution (calculated as the element) of a platinum-divinyltetramethyldisiloxane in dimethylpolysiloxane having vinyldimethylsiloxy terminal groups is substituted for (acac-$C_7H_8$)Pt(acac). The procedure for preparing the catalyst is described in Example 6 of U.S. Pat. No. 3,814,730.

To a mixture containing 10 parts of $H_2PtCl_6 \cdot 6H_2O$ and 20 parts of 1,3-divinyl-1,1,3,3-tetramethyldisiloxane and 50 parts ethanol, was added 20 parts of sodium bicarbonate. For 30 minutes the mixture was refluxed under constant agitation and then allowed to stand for 15 hours. After filtration the volatile components were removed from the filtrate by distillation at approximately 12 mm Hg (abs.). The residue was dissolved in benzene and the solution filtered and the benzene removed from the filtrate by distillation. The residue was then dissolved in dimethylpolysiloxane having vinyldimethylsiloxy terminal groups and a viscosity of 1400 cP at 23° C. at a rate so that the solution contains 1 percent platinum, calculated as the element.

At room temperature, the elapsed time between the initial addition of mixture B to mixture A and observable cross-linking was 2 minutes and 10 seconds.

Comparison Example b

The process described in Example 1 was repeated except that 1.6 grams of a 1 percent platinum solution (calculated as element) of (PtCl$_2$.C$_2$H$_4$)$_2$ in methylene chloride (described in U.S. Pat. No. 3,159,601) is substituted for (acac-C$_7$H$_8$)Pt(acac).

At room temperature, the elapsed time between the initial incorporation of mixture B in mixture A and observable crosslinking of the composition was 10 minutes.

Comparison Example c

The procedure described in Example 1 was repeated, except that 1.6 grams of a 1 percent platinum solution (calculated as the element) of platinum-(II)-diacetylacetonate in methylenechloride (described in U.S. Pat. No. 3,723,497) was substituted for the (acac-C$_7$H$_8$)Pt(acac).

At room temperature, the elapsed time between the initial incorporation of mixture B in mixture A and observable crosslinking of the composition was 3 hours.

In view of the fact that unlike platinum-divinyltetramethyldisiloxane, described in U.S. Pat. No. 3,814,730, the complex [(CH$_3$O—C$_{10}$H$_{12}$)PtCl]$_2$ contains inorganic halogen and in view of the fact that platinum-(II)-diacetylacetonate is very slow at room temperature, it is surprising that the aforementioned [(CH$_3$O—C$_{10}$H$_{12}$)PtCl]$_2$ and the acetylacetonate type complexes of this invention are so effective.

What is claimed is:

1. An improved process for effecting the addition of silicon-bonded hydrogen atoms to compounds containing aliphatic multiple bonds in the presence of a platinum catalyst, the improvement which comprises contacting a compound containing at least one silicon-bonded hydrogen atom with a compound containing aliphatic carbon atoms linked by multiple bonds in the presence of a platinum catalyst selected from the group consisting of

| | | |
|---|---|---|
| I | XPtY, | |
| II | 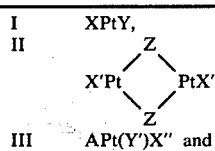 | |
| III | APt(Y')X" and | | mixtures thereof, in which A is halogen, X is a hydrocarbon radical having from 1 to 3 aliphatic double bonds which is bonded to the platinum atom via a PtC-sigma bond and a Pt-olefin-Pi-bond, X' is a hydrocarbon radical substituted with an alkoxy or acyloxy group and has from 1 to 3 double bonds and is bonded to the platinum atom via a PtC-sigma bond and a Pt-olefin-Pi-bond, X" is a hydrocarbon having an aliphatic double bond which is bonded to the platinum atom via a Pt-olefin-Pi-bond, Y is a chelated beta-diketonate ligand or arylcarboxylate ligand, Y' is a beta-diketonate ligand and Z is a double link bridge ligand.

2. The improved process of claim 1, wherein the platinum catalyst has the formula:

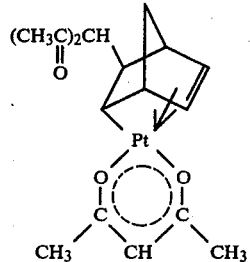

3. The improved process of claim 1, wherein the platinum catalyst has the formula:

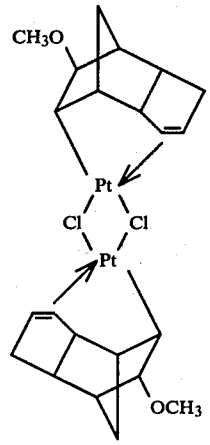

4. The improved process of claim 1, wherein the platinum catalyst is acetylacetonatechloro(ethylene)-platinum-(II).

5. The improved process of claim 1, wherein the addition is affected at a temperature up to 150° C.

6. An improved process for curing an organopolysiloxane containing alkenyl groups and an organopolysiloxane containing silicon bonded hydrogen atoms in the presence of a platinum catalyst, the improvement which comprises mixing the alkenyl containing organopolysiloxane with the silicon bonded hydrogen containing organopolysiloxane in the presence of a platinum catalyst selected from the group consisting of

| | |
|---|---|
| XPtY, | I |
| 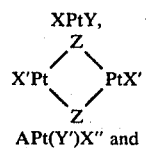 | II |
| APt(Y')X" and | III | mixtures thereof, in which A is a halogen, X is a substituted or unsubstituted hydrocarbon radical having from 1 to 3 aliphatic double bonds which is bonded to the platinum atom via a PtC-sigma bond and a Pt=olefin-Pi-bond, X' is a hydrocarbon radical which is substituted with an alkoxy or acyloxy group and has from 1 to 3 double bonds and is bonded to the platinum atom via a PtC-sigma bond and a Pt-olefin-Pi-bond, X″ is a substituted or unsubstituted hydrocarbon having an aliphatic double bond which is bonded to the platinum atom via a Pt-olefin-Pi-bond, Y is a chelated beta-diketonate ligand or arylcarboxylate ligand, Y′ is a beta-diketonate ligand and Z is a double link bridge ligand.

7. The improved process of claim 6, wherein the platinum catalyst has the formula:

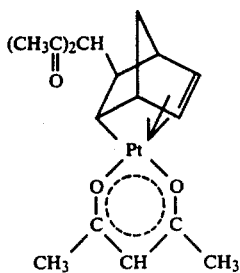

8. The improved process of claim 6, wherein the platinum catalyst has the formula:

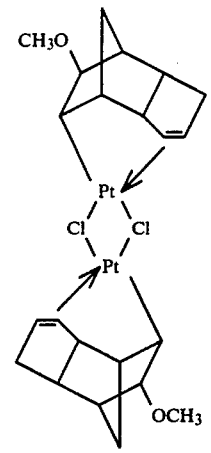

9. The improved process of claim 6, wherein the platinum catalyst is acetylacetonatechloro(ethylene)-platinum-(II).

10. The improved process of claim 6, wherein the organopolysiloxane contains at least two alkenyl groups per molecule and the organohydrogenpolysiloxane contains at least three silicon bonded hydrogen atoms per molecule.

11. A improved process for preparing a dental impression which comprises applying a mixture containing an organopolysiloxane having alkenyl groups and an organohydrogenpolysiloxane containing silicon bonded hydrogen atoms and a platinum catalyst to a tooth of which an impression is to be taken, curing the material and thereafter removing the resultant impression from the tooth, the improvement which comprises using as a platinum catalyst a catalyst selected from the group consisting of

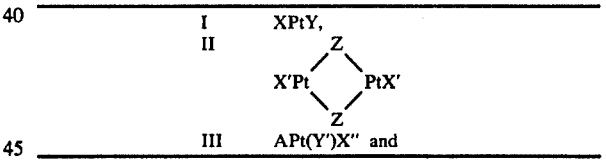

mixtures thereof, in which A is halogen, X is a hydrocarbon radical having from 1 to 3 aliphatic double bonds which is bonded to the platinum atom via a PtC-sigma bond and a Pt-olefin-Pi-bond, X′ is a hydrocarbon radical substituted with an alkoxy or acyloxy group and has from 1 to 3 double bonds and is bonded to the platinum atom via a PtC-sigma bond and a Pt-olefin-Pi-bond, X″ is a hydrocarbon having an aliphatic double bond which is bonded to the platinum atom via a Pt-olefin-Pi-bond, Y is a chelated beta-diketonate ligand or arylcarboxylate ligand, Y′ is a beta-diketonate ligand and Z is a double link bridge ligand.

* * * * *